United States Patent [19]
Romero et al.

[11] Patent Number: 6,103,766
[45] Date of Patent: *Aug. 15, 2000

[54] PHENYLSULFONAMIDE-PHENYLETHYLAMINES USEFUL AS DOPAMINE RECEPTORS

[75] Inventors: Arthur Glenn Romero; Jeffrey A. Leiby, both of Kalamazoo, Mich.

[73] Assignee: Pharmacia & Upjohn Company, Kalamazoo, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 09/306,748

[22] Filed: May 7, 1999

Related U.S. Application Data

[60] Provisional application No. 60/085,493, May 14, 1998.
[51] Int. Cl.$^7$ ..................... A61K 31/275; A61K 31/18; A61K 31/165
[52] U.S. Cl. ............... 514/604; 514/524; 514/602; 514/603; 514/810; 514/812; 514/923; 558/413; 564/85; 564/86; 564/89; 564/92
[58] Field of Search .................... 514/524, 602, 514/603, 604, 810, 812, 923; 558/413; 564/85, 86, 89, 92

[56] References Cited

U.S. PATENT DOCUMENTS 3,574,741  4/1971  Gould ........................... 564/92

FOREIGN PATENT DOCUMENTS

| 0 611 003 A1 | 8/1994 | European Pat. Off. | C07C 311/21 |
|---|---|---|---|
| WO 95/21165 | 8/1995 | WIPO | C07D 401/14 |
| WO 96/16040 | 5/1996 | WIPO | C07D 233/54 |
| WO 97/43262 | 11/1997 | WIPO | C07D 217/04 |
| WO 98/03473 | 1/1998 | WIPO | C07C 237/16 |

OTHER PUBLICATIONS

Ice, R.D., et al., "*Concentration of Dopamine Analogs in the Adrenal Medulla,*" J. of Nuclear Medicine 16(12):1147–1151 [1975].
Kato, H. et al., "*1–(Substituted aryl)alkyl–1H–imidazopyridin–4–amines as interferon inducers,*" CA 130–291590, [Mar. 26, 1999].
Baxter, E.W. et al., "*Arylsulfonate Esters in Solid Phase Organic Synthesis. II. Compatibility with Commonly–Used Reaction Conditions,*" Tetrahedron Letters 39:979–982 [1998].
Sokoloff, P., et al., "*Molecular cloning and characterization of a novel dopamine receptor ($D_3$) as a target for neuroleptics,*" Nature 347:146–151 [1990].

*Primary Examiner*—Peter O'Sullivan
*Attorney, Agent, or Firm*—Lucy X. Yang; Donald L. Corneglio

[57] ABSTRACT

Compounds of Formula I and their pharmaceutically acceptable salts having selective dopamine D3 receptor activity suitable for treating central nervous system disorders. Formula I:

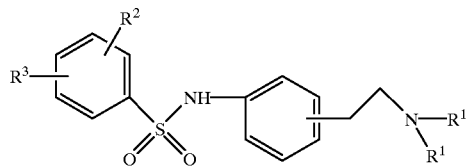

$R_1$ is independently H or a $C_1$–$C_8$ alkyl including isomeric forms thereof;

$R_2$ is H, $C_1$–$C_3$ alkyl, a halogen, $OCH_3$, $OCF_3$, $CF_3$, CN, $SCH_3$ or $NHCOCH_3$; and $R_3$ is H, $C_1$–$C_3$ alkyl, a halogen, $OCH_3$, $OCF_3$, $CF_3$, CN, $SCH_3$ or $NHCOCH_3$.

9 Claims, No Drawings

PHENYLSULFONAMIDE-PHENYLETHYLAMINES USEFUL AS DOPAMINE RECEPTORS

CROSS REFERENCE TO RELATED APPLICATIONS

This application claims the benefit of U.S. Ser. No. 60/085,493, filed May 14, 1998, under 35 USC 119(e)(i).

BACKGROUND OF THE INVENTION

The subject invention is directed toward a novel phenylsulfonamide-(phenylethylamine) chemical structure wherein the phenylsulfonamide is optionally substituted. The compound and its pharmaceutically acceptable salts preferentially bind to the dopamine D3 receptor and therefore are useful in the treatment of CNS diseases such as schizophrenia, Parkinson's disease, tardive dyskinesia, obsessive compulsive disorder, depression, and anxiety.

The dopamine D3 receptor was recently cloned by Sokoloff et al. (Nature, 347, 146 (1990)). It was hypothesized that this receptor subtype is of importance for the action of anti-psychotics. Interestingly, this receptor shows a relatively high abundance in brain regions associated with emotional and cognitive functions.

Compounds with this profile may be useful in treating CNS disorders, e.g. schizophrenia, mania, depression, geriatric disorders, drug abuse and addiction, Parkinson's disease, anxiety disorders, sleep disorders, circadian rhythm disorders and dementia.

SUMMARY OF THE INVENTION

In one aspect the subject invention is directed toward compounds and pharmaceutically acceptable salts of Formula I:

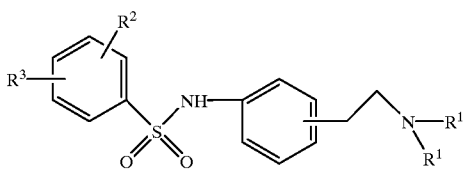

$R_1$ is independently H or a $C_1$–$C_8$ alkyl including isomeric forms thereof;

$R_2$ is H, $C_1$–$C_3$ alkyl including isomeric forms thereof, halogens (preferably, Cl, F and Br), $OCH_3$, $OCF_3$, $CF_3$, CN, $SCH_3$ or $NHCOCH_3$; and $R_3$ is H, $C_1$–$C_3$ alkyl including isomeric forms thereof, halogens (preferably, Cl, F and Br), $OCH_3$, $OCF_3$, $CF_3$, CN, $SCH_3$ or $NHCOCH_3$.

In Formula I, the ethylamine moiety is depicted to be at either the meta or para position to form either isomer.

In yet another aspect the subject invention is a method for treating schizophrenia by administering a therapeutically effective amount of a compound of Formula I to a patient suffering from schizophrenia. The compounds of Formula I can be administered to a patient suffering from schizophrenia, mania, depression, geriatric disorders, drug abuse and addiction, Parkinson's disease, sleep disorders, circadian rhythm disorders, anxiety disorders or dementia. The compounds can be administered in an amount of from about 0.25 mg to about 100 mg/person.

In yet another aspect, the subject invention is directed toward a method for treating central nervous system disorders associated with the dopamine D3 receptor activity in a patient in need of such treatment comprising administering to the subject a therapeutically effective amount of a Formula I compound for alleviation of such disorder. Typically, the compound of Formula I is administered in the form of a pharmaceutical composition comprising a pharmaceutically-acceptable carrier or diluent.

In yet another aspect, the subject invention is directed toward a pharmaceutical composition for treating central nervous system disorders associated with the dopamine D3 receptor activity comprising an effective amount of a compound of Formula I with a pharmaceutically-acceptable carrier or diluent.

DETAILED DESCRIPTION OF THE INVENTION

The subject invention is directed toward compounds or pharmaceutically acceptable salts of Formula I as depicted above in either racemic or pure enantiomer forms. The compounds are selective for the dopamine D3 receptor and have only modest affinity for the dopamine D2 receptor.

"Alkyl" are one to eight or three as specified carbon atoms such as methyl, ethyl, propyl, butyl, pentyl, hexyl, heptyl, octyl and isomeric forms thereof.

"Halogens" means the atoms fluorine, chlorine, bromine and iodine.

Pharmaceutically acceptable salts include salts of both inorganic and organic acids. The preferred pharmaceutically acceptable salts include salts of the following acids: methanesulfonic, hydrochloric, hydrobromic, sulfuric, phosphoric, nitric, benzoic, citric, tartaric, fumaric or maleic.

The compounds of Formula I are active orally or parenterally. Orally the Formula I compounds can be given in solid dosage forms such as tablets or capsules, or can be given in liquid dosage forms such as elixirs, syrups or suspensions as is known to those skilled in the art. It is preferred that the Formula I compounds be given in solid dosage form and that it be a tablet.

Typically, the compounds of Formula I can be given in the amount of about 0.5 mg to about 250 mg/person, one to three times a day. Preferably, about 5 to about 50 mg/day in divided doses.

The exact dosage and frequency of administration depends on the particular compound of Formula I used, the particular condition being treated, the severity of the condition being treated, the age, weight, general physical condition of the particular patient, other medication the individual may be taking as is well known to those skilled in the art and can be more accurately determined by measuring the blood level or concentration of the active compound in the patient's blood and/or the patient's response to the particular condition being treated.

Thus, the subject compounds, along with a pharmaceutically-acceptable carrier, diluent or buffer, can be administrated in a therapeutic or pharmacological amount effective to alleviate the central nervous system disorder with respect to the physiological condition diagnosed. The compounds can be administered intravenously, intramuscularly, topically, transdermally such as by skin patches, buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar pharmaceutical diluent or carrier materials. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions, the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

Binding Data for Examples

Competition binding experiments employed eleven dilutions of test compounds of Formula I competing with [$^3$H]-5-(dipropylamino)-5,6-dihydro-4H-imidazo(4,5,1-ij)quinolin-2(1H)-one (R-enantiomer) ("86170") (62 Ci/mmol, 2nM) and [$^3$H]-spiperone ("SPI") (107 Ci/mmol, 0.5 nM) for D2 and D3 binding sites, respectively. (Lahti, R. A., Eur. J. Pharmacol., 202, 289 (1991)) In each experiment, cloned rat receptors expressed in CHO-K1 cells were used. (Chio, C. L., Nature, 343, 266 (1990); and Huff, R. M., Mol. Pharmacol. 45, 51–60 (1993)). The results are shown in Table I.

TABLE I

| RECEPTOR BINDING DATE IC50 VALUES | | |
|---|---|---|
| Example # | Receptor | Ki (nM) |
| 1 | D2-DOP-CLONE | 629 |
|   | D3-DOP-CLONE | 3.7 |
| 2 | D2-DOP-CLONE | 1069 |
|   | D3-DOP-CLONE | 34 |
| 3 | D2-DOP-CLONE | 760 |
|   | D3-DOP-CLONE | 14, 26 |
| 4 | D2-DOP-CLONE | 677 |

TABLE I-continued

| RECEPTOR BINDING DATE IC50 VALUES | | |
|---|---|---|
| Example # | Receptor | Ki (nM) |
|   | D3-DOP-CLONE | 18 |
| 5 | D2-DOP-CLONE | 2390 |
|   | D3-DOP-CLONE | 28 |
| 6 | D2-DOP-CLONE | 2176 |
|   | D3-DOP-CLONE | 165 |
| 7 | D2-DOP-CLONE | 623 |
|   | D3-DOP-CLONE | 14 |
| 8 | D2-DOP-CLONE | 1529 |
|   | D3-DOP-CLONE | 33 |
| 9 | D2-DOP-CLONE | 645 |
|   | D3-DOP-CLONE | 54 |
| 10 | D2-DOP-CLONE | 1075 |
|   | D3-DOP-CLONE | 111 |

Scheme I

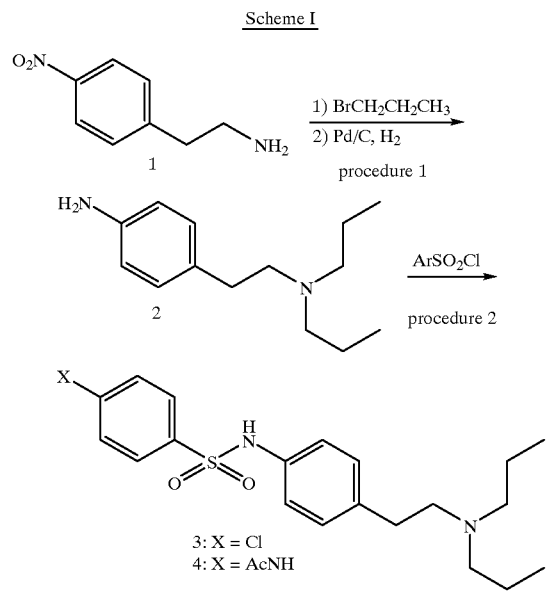

Scheme 2

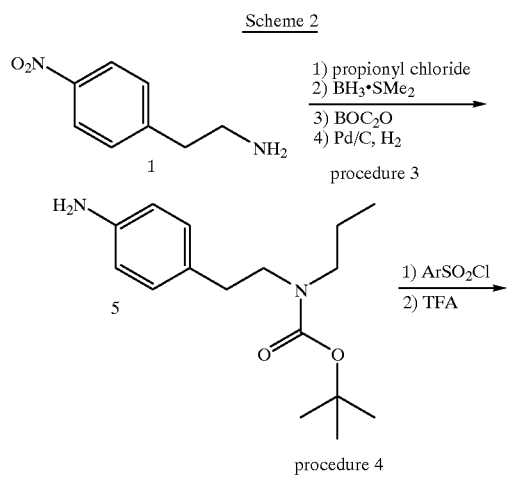

-continued

| | X | Y |
|---|---|---|
| 6: | Cl | Cl |
| 7: | Cl | H |
| 8: | F₃CO | H |
| 9: | F | Cl |
| 10: | Br | H |
| 11: | F₃C | H |

Scheme 3

12

1) CH$_3$SO$_2$Cl
2) H$_2$NCH$_2$CH$_2$CH$_3$
3) BOC$_2$O
4) Pd/C, H$_2$ procedure 5

13

1) ArSO$_2$Cl
2) TFA procedure 4

14: X = H, Y = F
15: X = Cl, Y = H

In procedure 1 (scheme 1), 4-nitrophenethylamine (1) was dipropylated with bromopropane followed by palladium-on-carbon catalytic hydrogenation of the nitro moiety to afford 2. Functionalization of the aromatic amine with arylsulfonyl chlorides using procedure 2 gived dipropylamine analogs 3 and 4.

Monopropyl amine analogs were synthesized using procedures 3 and 4 as shown in scheme 2. In procedure 3, 4-nitrophenethylamine (1) was acylated with propionyl chloride and this amide selectively reduced with borane. The resultant secondary amine was protected as the BOC-carbamate followed by palladium-on-carbon catalytic hydrogenation of the nitro moiety to afford 5. Using procedure 4, the aromatic amine was treated with arylsulfonyl chlorides followed by BOC-deprotection of the secondary amine with trifluoroacetic acid to give monopropylamine analogs 6, 7, 8, 9, 10, and 11.

Meta-substituted phenethylamines were synthesized using procedures 5 and 4 as shown in scheme 3. In procedure 5, 3-nitrophenethylalcohol (12) was sulfonylated with methanesulfonyl chloride and used to alkylate 1-aminopropane. The resultant secondary amine was protected as the BOC-carbamate followed by palladium-on-carbon catalytic hydrogenation of the nitro moiety to afford 13. Using procedure 4, the aromatic amine was treated with arylsul- fonyl chlorides followed by BOC-deprotection of the secondary amine with trifluoroacetic acid to give monopropylamine analogs 14 and 15.

EXAMPLE 1

Procedure 1: Preparation of 2-(4-aminophenyl)ethyl-1-dipropylamine (2)

2-(4-Nitrophenyl)ethylamine hydrochloride (3.9 g), potassium carbonate (2 eq), bromopropane (6 eq), and dimethylformamide (40 mL) were stirred at room temperature overnight. Solvent was concentrated under vacuum and the residue was partitioned between diethyl ether and water. The ether layer was washed with brine and solvent was removed under vacuum. The residue was flash chromatographed (dichloromethane/ ethyl acetate/ hexane) to give 2.9 g of an oil. This oil was catalytically hydrogenated in ethanol with 10% palladium-on-carbon to give 2.2 g of the title compound as an oil.

Procedure 2: Preparation of 2-[4-(4-chlorobenzenesulfonamido)phenyl]ethyl-1-dipropylamine (3)

4-Chlorobenzenesulfonyl chloride (0.40 g) in THF (3 mL) was added to 2-(4-aminophenyl)ethyl-1-dipropylamine (0.40 g), triethylamine (3 eq), and THF (5 mL). After 16 hours, it was partitioned between diethyl ether and saturated aqueous sodium bicarbonate. The ether layer was washed with brine and solvent was removed under vacuum. The residue was flash chromatographed (dichloromethane/ ethyl acetate/ hexane) to give 0.6 g of the title compound as an oil. The hydrochloride salt was crystallized from methanol/ diethyl ether to give a solid, m.p. 74–78° C.

EXAMPLE 2

Preparation of 2-[4-(4-acetamidobenzenesulfonamido)phenyl]ethyl-1-dipropylamine (4)

4-Acetamidobenzenesulfonyl chloride was added to 2-(4-aminophenyl)ethyl- 1-dipropylamine using procedure 2 to give the title compound. The hydrochloride salt was crystallized from methanol/diethyl ether to give a solid, m.p. 248–250° C.

Procedure 3: Preparation of 2-(4-aminophenyl)ethyl-1-(tert-butoxycarbonyl)propylamine (5)

Propionyl chloride (2.5 mL) was added to 2-(4-nitrophenyl)ethylamine hydrochloride (5.0 g), triethylamine (2.5 eq), and THF (50 mL). After 18 hours, the solution was partitioned between diethyl ether and water and the ether layer was washed with 2N hydrochloric acid, water, aqueous bicarbonate, and brine. Solvent was removed under vacuum and the residue was flash chromatographed (methanol/ dichloromethane) to give 3.3 g of a solid. This was dissolved in THF, borane-dimethyl sulfide (1.5 eq) was added, and it was refluxed 17 hours. It was then refluxed with 2N hydrochloric acid (20 mL) for 75 minutes and the mixture was extracted with diethyl ether. The aqueous layer was basified with sodium hydroxide and this basic aqueous layer was extracted with diethyl ether/ THF and the ether layer was washed with brine. Solvent was removed under vacuum to give 3.1 g of an oil. To this oil was added THF (40 mL) and di-tert-butyldicarbonate (1.1 eq). After 45 minutes, solvent was removed under vacuum and the residue was flash chromatographed (dichloromethane/ethyl acetate/ hexane)

to give 4.4 g of an oil. This oil was catalytically hydrogenated in ethanol with 10% palladium-on-carbon to give 3.7 g of the title compound as an oil.

EXAMPLE 3

Procedure 4: Preparation of 2-[4-(2,4-dichlorobenzenesulfonamido)phenyl]ethyl-1-propylamine (6)

2,4-Dichlorobenzenesulfonyl chloride (0.49 g) was added to 2-(4-aminophenyl)ethyl-1-(tert-butoxycarbonyl) propylamine (0.50 g), triethylamine (1.5 eq), and THF (5 mL). After 19 hours, it was partitioned between diethyl ether and saturated aqueous sodium bicarbonate. The ether layer was washed with brine and solvent was removed under vacuum. The residue was flash chromatographed (dichloromethane/ethyl acetate/hexane) to give 0.6 g of a solid. Trifluoroacetic acid (3 mL) was added; after 90 minutes it was removed under vacuum and the residue was partitioned between diethyl ether/THF and saturated aqueous sodium bicarbonate. The ether layer was washed with brine, solvent was removed under vacuum, and the residue was flash chromatographed (ammonium hydroxide in methanol/dichloromethane) to give the title compound as a solid, m.p. 165–168° C.

EXAMPLE 4

Preparation of 2-[4-(4-chlorobenzenesulfonamido)phenyl]ethyl-1-propylamine (7)

Using procedure 4, 4-chlorobenzenesulfonyl chloride was added to 2-(4-aminophenyl)ethyl-1-(tert-butoxycarbonyl) propylamine to give the title compound as a solid, m.p. 137–140° C.

EXAMPLE 5

Preparation of 2-[4-(4-trifluoromethoxybenzenesulfonamido)phenyl]ethyl-1-propylamine (8)

Using procedure 4, 4-trifluoromethoxybenzenesulfonyl chloride was added to 2-(4-aminophenyl)ethyl-1-(tert-butoxycarbonyl)propylamine to give the title compound as a solid, m.p. 151–154° C.

EXAMPLE 6

Preparation of 2-[4-(2-chloro-4-fluorobenzenesulfonamido)phenyl]ethyl-1-propylamine (9)

Using procedure 4, 2-chloro-4-fluorobenzenesulfonyl chloride was added to 2-(4-aminophenyl)ethyl-1-(tert-butoxycarbonyl)propylamine to give the title compound as a solid, m.p. 165–167° C.

EXAMPLE 7

Preparation of 2-[4-(4-bromobenzenesulfonamido)phenyl]ethyl-propylamine (10)

Using procedure 4, 4-bromobenzenesulfonyl chloride was added to 2-(4-aminophenyl)ethyl-1-(tert-butoxycarbonyl) propylamine to give the title compound as a solid, m.p. 141–143° C.

EXAMPLE 8

Preparation of 2-[4-[(4-trifluoromethyl)benzenesulfonamido]phenyl]ethyl-1-propylamine (11)

Using procedure 4, 4-(trifluoromethyl)benzenesulfonyl chloride was added to 2-(4-aminophenyl)ethyl-1-(tert-butoxycarbonyl)propylamine to give the title compound as a solid, m.p. 172–174° C.

EXAMPLE 9

Preparation of 2-[3-(2-fluorobenzenesulfonamido)phenyl]ethyl-1-propylamine (12)

Using procedure 4, 2-fluorobenzenesulfonyl chloride was added to 2-(3-aminophenyl)ethyl-1-(tert-butoxycarbonyl) propylamine (13) to give the title compound as a solid, m.p. 165–169° C.

EXAMPLE 10

Preparation of 2-[3-(3-chlorobenzenesulfonamido)phenyl]ethyl-1-propylamine (13)

Using procedure 4, 3-chlorobenzenesulfonyl chloride was added to 2-(3-aminophenyl)ethyl-1-(tert-butoxycarbonyl) propylamine (13) to give the title compound as a solid, m.p. 145–148° C.

Procedure 5: Preparation of 2-(3-aminophenyl) ethyl-1-(tert-butoxycarbonyl)propylamine (13)

Triethylamine (1.2 eq) and methanesulfonyl chloride (1.1 eq) were added to 2-(3-nitrophenyl)ethyl alcohol (5.0 g) in acetonitrile (60 mL) in an ice bath. After 25 minutes propylamine (10 eq) was added and the solution was refluxed for 15 hours. Solvent was removed under vacuum; the hydrochloric acid salt was made and then crystallized from ethanol/hexane. To this was added THF (70 mL), triethylamine (1.1 eq), and di-tert-butyldicarbonate (1.1 eq). After 60 minutes, solvent was removed under vacuum and the residue was partitioned between 2N hydrochloric acid and diethyl ether. The ether layer was washed with water, aqueous sodium bicarbonate, and brine, and the solvent was removed under vacuum. The residue was flash chromatographed (ethyl acetate/hexane) to give 10.9 g of an oil. This oil was catalytically hydrogenated in ethanol with 10% palladium-on-carbon to give 7.8 g of the title compound as an oil.

What is claimed:

1. A compound of structural Formula I or its pharmaceutically acceptable salts:

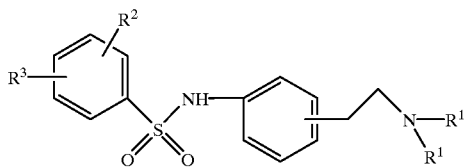

$R_1$ is independently H or a $C_1$–$C_8$ alkyl;

$R_2$ is H, $C_1$–$C_3$ alkyl, a halogen, $OCH_3$, $OCF_3$, $CF_3$, CN, $SCH_3$ or $NHCOCH_3$; and $R_3$ is H, $C_1$–$C_3$ alkyl, a halogen, $OCH_3$, $OCF_3$, $CF_3$, CN, $SCH_3$ or $NHCOCH_3$ with the proviso at least one $R^1$ is C1–C8 alkyl; with the further proviso that when $r^2$ and $r^3$ are both hydrogen then the $R^1$'s are both C1–C8 alkyl; and with the further proviso that when one of $R^2$ and $r^3$ is p-methoxy, and the other is hydrogen, then the $R^1$'s cannot both be ethyl.

2. The compound of claim 1 wherein said $R_1$'s are independently H or $C_{1-6}$ alkyl.

3. The compound of claim 2 wherein one of said $R_1$ is propyl.

4. The compound of claim 1 wherein said $R_2$ and $R_3$ are both Cl.

5. The compound of claim 1 wherein said $R_2$ is hydrogen and said $R_3$ is Cl.

6. The compound of claim 1 wherein said $R_2$ is hydrogen and said $R_3$ is —$OCF_3$.

7. The compound of claim 1 which is:
   a) 2-[4-(4-chlorobenzenesulfonamido)phenyl]ethyl-1-dipropylamine;
   b) 2-[4-(4-acetamidobenzenesulfonamido)phenyl]ethyl-1-dipropylamine;
   c) 2-[4-(2,4-dichlorobenzenesulfonamido)phenyl]ethyl-1-propylamine;
   d) 2-[4-(4-chlorobenzenesulfonamido)phenyl]ethyl-1-propylamine;
   e) 2-[4-(4-trifluoromethoxybenzenesulfonamido)phenyl]ethyl-1-propylamine;
   f) 2-[4-(2-chloro-4-fluorobenzenesulfonamido)phenyl]ethyl-1-propylamine;
   g) 2-[4-(4-bromobenzenesulfonamido)phenyl]ethyl-1-propylamine;
   h) 2-[4-[(4-trifluoromethyl)benzenesulfonamido]phenyl]ethyl-1-propylamine;
   i) 2-[3-(2-fluorobenzenesulfonamido)phenyl]ethyl-1-propylamine; or
   j) 2-[3-(3-chlorobenzenesulfonamido)phenyl]ethyl-1-propylamine.

8. The compound of claim 1, wherein said $R^2$ is hydrogen and said $R^3$ is –$CF_3$.

9. A method for treating central nervous system disorders associated with dopamine D3 receptor activity comprising:
   administering to a patient in need thereof a therapeutically effective amount of a compound of Formula I of claim 1.

* * * * *